United States Patent [19]

Smith

[11] Patent Number: 5,087,740

[45] Date of Patent: Feb. 11, 1992

[54] PROCESS FOR PURIFYING N-PHOSPHONOMETHYLGLYCINE

[75] Inventor: Lowell R. Smith, Kirkwood, Mo.

[73] Assignee: Monsanto Company, St. Louis, Mo.

[21] Appl. No.: 561,483

[22] Filed: Jul. 30, 1990

Related U.S. Application Data

[63] Continuation of Ser. No. 394,998, Aug. 17, 1989, abandoned.

[51] Int. Cl.$^5$ ................................................ C07F 9/38
[52] U.S. Cl. ..................................................... 562/17
[58] Field of Search ......................................... 562/17

[56] References Cited

U.S. PATENT DOCUMENTS

| | | | |
|---|---|---|---|
| 4,197,254 | 4/1980 | Gaertner | 562/17 |
| 4,439,428 | 3/1984 | Cox | 71/86 |
| 4,605,522 | 8/1986 | Robbins | 260/502.5 |
| 4,684,483 | 8/1987 | Richard et al. | 562/17 |

FOREIGN PATENT DOCUMENTS 127415 11/1978 Japan.

Primary Examiner—J. E. Evans
Attorney, Agent, or Firm—Frank D. Shearin

[57] ABSTRACT

N-Phosphonomethylglycine can be purified and concentrated from aqueous solutions containing N-phosphonomethylglycine and impurities, such as N-formyl-N-phosphonomethylglycine, phosphorous acid, and the like, by passing the aqueous solution through an ion exchange column containing a weakly basic ion exchange resin to remove such impurities.

8 Claims, No Drawings

PROCESS FOR PURIFYING N-PHOSPHONOMETHYLGLYCINE

This is a continuation of application Ser. No. 07/394,998, filed on Aug. 17, 1989, now abandoned.

BACKGROUND OF THE INVENTION

This invention relates to a method for purifying and concentrating N-phosphonomethylglycine in an aqueous solution containing impurities using weakly basic ion exchange resin.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-Phosphonomethylglycine and its salts are conveniently applied in an aqueous formulation as a postemergent phytotoxicant for the control of numerous plant species. N-Phosphonomethylglycine and its salts are characterized by a broad spectrum activity, i.e. the control growth of a wide variety of plants.

Numerous methods are known in the art for the preparation of N-phosphonomethylglycine. For example, U.S. Pat. No. 3,969,398 to Hershman discloses a process for the production of N-phosphonomethylglycine by the oxidation of N-phosphonomethyliminodiacetic acid utilizing a molecular oxygen-containing gas as the oxidant in the presence of a catalyst consisting essentially of activated carbon. U.S. Pat. No. 3,954,848 to Franz discloses the oxidation of N-phosphonomethyliminodiacetic acid with hydrogen peroxide and an acid such as sulfuric acid. U.S. Pat. No. 4,670,190 to Kleiner discloses a process for the preparation of N-phosphonomethylglycine by reacting aminomethylphosphonic acid and glyoxylic acid in a molar ratio of about 1 to 2 in an aqueous medium or aqueous organic medium at temperatures between 30° and 100° C. These references are only illustrative, since there are many other methods known in the art for preparing N-phosphonomethylglycine.

Regardless of the process by which N-phosphonomethylglycine is prepared, all of these processes produce aqueous streams, including waste streams, that contain N-phosphonomethylglycine and various by-products and unreacted starting materials, for example, N-phosphonomethyliminodiacetic acid, N-formyl-N-phosphonomethylglycine, phosphoric acid, phosphorous acid, hexamethylenetetraamine, aminomethylphosphonic acid, iminodiacetic acid, formaldehyde, formic acid, and the like. Because of the valuable nature of the N-phosphonomethylglycine, it can be seen that there is a need among those skilled in the art to be able to recover the valuable N-phosphonomethylglycine from such aqueous streams by purifying the N-phosphonomethylglycine and recycling the other products to an earlier stage of the process for further conversion to the desired N-phosphonomethylglycine, or discharging such aqueous streams to waste treatment facilities and recovering the N-phosphonomethylglycine before it is so discharged.

Now, according to the present invention, there is provided a method of purifying and concentrating the N-phosphonomethylglycine in the presence of more acidic and basic compounds in the aqueous streams. In one embodiment of this invention, there is provided a method of concentrating and purifying the N-phosphonomethylglycine in the aqueous streams by first separating the components that are more acidic than N-phosphonomethylglycine, and thereafter separating the N-phosphonomethylglycine from those components that are less acidic than N-phosphonomethylglycine.

SUMMARY OF THE INVENTION

These and other advantages are achieved by a method of obtaining purified N-phosphonomethylglycine from aqueous solutions containing impurities which comprises passing the aqueous solution through an ion exchange column containing a weakly basic ion exchange resin to remove impurities in the aqueous solution that are more acidic than N-phosphonomethylglycine.

DETAILED DESCRIPTION OF THE INVENTION

According to the present invention, an aqueous stream in a process to prepare N-phosphonomethylglycine, or an aqueous waste stream from the N-phosphonomethylglycine manufacturing process, will contain varying amounts of N-phosphonomethylglycine, depending upon the temperature of the aqueous stream and other factors. At 25° C., N-phosphonomethylglycine is soluble in water to the degree of about 1.3%. Such aqueous streams will contain other impurities from the manufacturing process, which may be unwanted by-products or unreacted starting materials. According to the method of the present invention, the aqueous stream containing such impurities are passed through ion exchange columns containing weakly basic ion exchange resins to remove the impurities that are more acidic and less acidic than N-phosphonomethylglycine. The N-phosphonomethylglycine in the aqueous stream from the effluent of the column can then be used directly as a herbicide, or processed further. The impurities retained on the weakly basic ion exchange resin can be removed by passing a dilute solution of a strong mineral acid, such as sulfuric acid or hydrochloric acid, through the column, as will occur to those skilled in the art.

The aqueous stream in a manufacturing process, or an aqueous stream as a waste stream, can contain any number of impurities, in addition to N-phosphonomethylglycine, depending upon the manufacturing process used. Examples of such impurities include compounds that are more acidic than N-phosphonomethylglycine such as, but not limited to, N-phosphonomethyliminodiacetic acid, N-formyl-N-phosphonomethylglycine, phosphoric acid, phosphorous acid, and the like. The aqueous stream can also contain impurities that are less acidic than N-phosphonomethylglycine such as, but not limited to, aminomethylphosphonic acid, iminodiacetic acid, formaldehyde, glycine, glyoxylic acid, and formic acid.

According to a preferred embodiment of this invention, there is provided a method of concentrating and purifying N-phosphonomethylglycine in an aqueous stream containing impurities selected from the group consisting of N-phosphonomethyliminodiacetic acid, N-formyl-N-phosphonomethylglycine, phosphoric acid, phosphorous acid, aminomethylphosphonic acid, iminodiacetic acid, formaldehyde, glycine, gloxylic acid and formic acid, which comprises: a) passing the process stream through a first ion exchange column containing the weakly basic ion exchange resin which retains impurities more acidic than N-phosphonomethylglycine, the impurities retained being selected from the group consisting of N-phosphonomethyliminodiacetic acid, N-formyl-N-phosphonomethylglycine, phosphoric acid, phosphorous acid and; b) passing the effluent from the first column through a second ion exchange column containing a weakly basic ion exchange resin until breakthrough of N-phosphonomethylglycine occurs; and thereafter, c) recovering the N-phosphonomethylglycine by passing through the second ion exchange column a base selected from the group consisting of alkali metal hydroxides, alkali metal carbonates, ammonium hydroxide, ammonium carbonate and primary or secondary organic amines having a molecular weight below about 300. The N-phosphonomethylglycine can also be recovered by passing through the second ion exchange column a strong mineral acid, such as sulfuric acid or hydrochloric acid. Hydrochloric acid is preferred.

Ion exchange columns are known to those skilled in the art. Typically, such ion exchange columns are closed cylindrical vessels having an inlet port at the top, an exit port at the bottom, and another port located near the middle of the column which is typically used to pass chemicals through the column to regenerate the resin. Such ion exchange columns are normally loaded to between half and two thirds of their volume with the ion exchange resin to permit expansion and contraction of the resin as it is being used or regenerated. The size of such ion exchange columns and the amount of resin to be used depends upon the volume of material that is to be processed. In the process of the present invention, no special configuration of ion exchange column is required, and as will occur to those skilled in the art in view of the present disclosure, the size of the ion exchange column or any particular configuration can be determined by those skilled in the art, depending on the volume of material to be processed.

The ion exchange resins for use in the process of the present invention are known to those skilled in the art. Broadly described, ion exchange is the reversible interchange of ions between a solid and liquid in which there is no permanent change in the structure of the ion exchange material. In 1935, the introduction of synthetic organic ion exchange resins resulted from the synthesis of phenolic condensation products containing either sulfonic or amine groups which could be used for the reversible exchange of cations or anions. Weakly basic ion exchange resins are obtained today in a variety of base strengths depending upon the nature of the amine functionality. Primary, secondary and tertiary amine functionality, or mixtures of them, can be put into various structures ranging from epichlorohydrin-amine condensates and acrylic polymers, to styrene-divinylbenzene copolymers. The ability of such weak base resins to absorb acids depends upon their basicity and the pKa of the acid involved. Since N-phosphonomethylglycine has a pKa value of about 2.2, any weakly basic ion exchange resin that has sufficient basicity to absorb N-phosphonomethylglycine and acids that have a pKa value of less than about 2.2 can be used in the process of the present invention.

Commercially available ion exchange resins that can be used in the process of the present invention include the weakly basic ion exchange resins sold by: Rohm & Haas Co. (Philadelphia, Pa.) under their Amberlite trademark such as AMBERLITE IRA-93, AMBERLITE IRA-94, AMBERLITE IRA-68 and AMBERLITE IRA-35; Diamond Shamrock Corp. (Dallas, Tex.) under their trademark DUOLITE A-392; and Sybron Chemicals, Inc. (Birmingham, N.J.) under their Ionac trademark such as IONAC 305, IONAC 365 and IONAC 380. Other commercially available ion exchange resins can be used as known to those skilled in the art.

In the process of the present invention, as the aqueous stream is passed through the weakly basic ion exchange resin, impurities that are more acidic than N-phosphonomethylglycine, such as N-phosphonomethyliminodiacetic acid, N-formyl-N-phosphonomethylglycine, phosphoric acid, phosphorous acid, and the like, are absorbed on the weakly basic ion exchange resin. As additional quantities of the aqueous stream are passed through the resin, the N-phosphonomethylglycine is displaced by the more acidic impurities, resulting in an effluent from the ion exchange resin of N-phosphonomethylglycine and impurities that are less acidic, such as aminomethylphosphonic acid, iminodiacetic acid, formaldehyde, formic acid, glycine, and the like. The method is continued until breakthrough of impurities that are more acidic than N-phosphonomethylglycine occurs, as determined by conductivity measurements, pH change, and the like. On the other hand, the method can be practiced by volumetric control of the amount of aqueous stream entering the ion exchange column.

When breakthrough occurs, the column can be regenerated by washing with water, and then with a dilute aqueous solution of a strong mineral acid, such as sulfuric acid or hydrochloric acid. As is known to those skilled in the art, strong oxidizing acids, such as hot nitric acid or chromic acid/nitric acid mixtures, should be avoided for regeneration, and certain metal ions, such as iron, manganese and copper, should be minimized in any oxidizing solution. Thereafter, a dilute base, such as a dilute sodium hydroxide solution, is passed through the column to complete the regeneration.

In one embodiment of this invention, an aqueous solution containing N-phosphonomethylglycine and various impurities are passed through an ion exchange column containing a weakly basic ion exchange resin until there is a breakthrough of impurities that are more acidic than N-phosphonomethylglycine. The effluent from the column can be collected and passed through an ion exchange column containing a weakly basic ion exchange resin, which can be either a separate column, or the same column that has been regenerated as described above. The effluent is passed through until there is a breakthrough of N-phosphonomethylglycine in the effluent. Then, the N-phosphonomethylglycine is recovered from the ion exchange resin by passing through the ion exchange column a strong mineral acid or a base to form a water soluble salt of N-phosphonomethylglycine.

Suitable bases that can be used include aqueous solutions of the alkali metal hydroxides, such as lithium hydroxide, sodium hydroxide, potassium hydroxide, and the like; alkali metal carbonates, such as sodium carbonate, potassium carbonate and the like; or ammonium hydroxide or ammonium carbonate. Organic amines that have a molecular weight below about 300 can also be used. Such organic amines include the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecyl amine, methyloctadecylamine, ethylbutylamine, ethylheptylamine, ethyloctylamine, hexylheptylamine, hexyloctylamine, dimethylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3- dimethylbutenyl-2-amine, di-butenyl-2-amine n-hexenyl-2-amine and propylenediamine, primary aryl amines such as aniline, methoxyaniline, ethoxyaniline, o,m,p-toluidine, phenylenediamine, 2,4, 6-tribromoaniline, benzidine, naphthylamine, o,m,p-chloroaniline, and the like; hetrocyclic amines such as pyridine, morpholine; piperidine, pyrrolidine, indoline, azepine and the like. Isopropylamine is preferred.

In the preferred embodiment of this invention, there is provided a method of concentrating and purifying N-phosphonomethylglycine in an aqueous solution containing impurities selected from the group consisting of N-phosphonomethyliminodiacetic acid, N-formyl-N-phosphonomethylglycine, phosphoric acid, phosphorous acid, hexamethylenetetramine, aminomethylphosphonic acid, iminodiacetic acid, formaldehyde, glycine, formic acid, and the like which comprises: a) passing the aqueous stream through a first ion exchange column containing a weakly basic ion exchange resin which retains impurities more acidic than N-phosphonomethylglycine, the impurities retained being selected from the group consisting of N-phosphonomethyliminodiacetic acid, N-formyl-N-phosphonomethylglycine, phosphoric acid, phosphorous acid, and the like; b) passing the effluent from the first column through a second ion exchange column containing a weakly basic ion exchange resin until breakthrough of N-phosphonomethylglycine occurs; and thereafter, c) recovering the N-phosphonomethylglycine from the weakly basic ion exchange resin by passing an aqueous solution of a alkali metal hydroxide, or an amine having a molecular weight of less than about 300, through the second column.

As will occur to those skilled in the art in view of the disclosure, the weakly basic ion exchange resins can be regenerated by techniques known to those skilled in the art, such as by passing dilute hydrochloric acid through the resins to remove the impurities contained on the resin, and thereafter treating the resin with dilute sodium hydroxide. The impurities can then be recycled, if desired, to the process for manufacturing N-phosphonomethylglycine, or can be discarded.

The invention is further illustrated by, but not limited to, the following examples. All percentages are by weight unless otherwise indicated.

EXAMPLES

Three aqueous solutions (1098.7 g., 1078.8 and 592.2 g) containing 1.89%, 1.41% and 1.49% N-phosphonomethylglycine (glyphosate), respectively, were passed through an ion exchange system consisting of one 80 ml. column of AMBERLITE IRA-93 ion exchange resin, and three 80 ml. columns of AMBERLITE IRA-68. The flow was stopped when the conductivity of the effluent from the second AMBERLITE IRA-68 column reached 4840 micromhos. Deionized water (600 ml.) was passed through the three AMBERLITE IRA-68 columns, and a solution (258.5 g.) of isopropylamine (3.3%) in water was passed through the first Amberlite IRA-68 column. When the solution was used up, additional water was added to the first Amberlite IRA-68 column. A product fraction (300 ml.) was collected, controlled by conductivity of the effluent, which contained 3.66% glyphosate. Additional water was added to the first AMBERLITE IRA-68 column and an afterrun (250 g.) was collected.

Valving was changed so that the first AMBERLITE IRA-68 column became the third in line, the second became first and the third became second. Process filtrates (542.2 g. and 266.0 g) containing 1.49 and 1.35% glyphosate, respectively, were passed through the four columns until the conductivity of the second column reached the specified valve. Water, isopropylamine solution and additional water were added to the AMBERLITE IRA-68 column first in line as described above. This produced a product fraction (300 ml.) containing 4.34% glyphosate.

During the above experiment the conductivity of the AMBERLITE IRA-93 columns effluent indicated that it was saturated with strong acids. Water, dilute hydrochloric acid, 3% sodium hydroxide solution and additional water was passed through the AMBERLITE IRA-93 column and it was returned to use.

Analytical data are showin in Table I.

TABLE I

| | COMPOSITIONS, % | | | | | | | | |
|---|---|---|---|---|---|---|---|---|---|
| | Glyphosate | N-Phosphono-methylimino-diacetic Acid | Form-aldehyde | Formic Acid | N-Methyl Glyphosate | N-formyl Glyphosate | Amino-methyl-Phosphonic Acid | Phosphate | Phosphite |
| Solutions (g) | | | | | | | | | |
| 1098.7 | 1.89 | 0.020 | 1.99 | 0.85 | 0.156 | 0.11 | 0.33 | 0.016 | 0.003 |
| 1078.8 | 1.41 | 0.005 | 2.00 | 0.87 | 0.074 | 0.076 | 0.36 | 0.069 | 0.007 |
| 592.2 | 1.49 | 0.005 | 2.12 | 0.94 | 0.081 | 0.076 | 0.37 | 0.021 | 0.003 |
| 542.2 | 1.49 | 0.005 | 2.12 | 0.94 | 0.081 | 0.076 | 0.37 | 0.021 | 0.003 |
| 266.0 | 1.35 | 0.003 | 2.01 | 0.92 | 0.069 | 0.076 | 0.35 | 0.022 | 0.004 |
| Products (g) | | | | | | | | | |
| 300 | 3.66 | | | 0.074 | 0.18 | 0.01 | 0.03 | 0.002 | |
| 300 | 4.34 | | | 0.101 | 0.31 | 0.025 | 0.06 | 0.005 | |

Although the invention has been described in terms of specified embodiments which are set forth in considerable detail, it is understood that this is by way of illustration only, and that alternative embodiments and operating techniques will become apparent to those skilled in the art in view of the disclosure. For example, one skilled in the art might change the conditions and procedures described herein and use a strongly basic ion exchange resin to concentrate and purify N-phosphonomethylglycine from an aqueous solution. Accordingly, modifications can be made without departing from the spirit of the described invention.

What is claimed is:

1. A method of obtaining purified N-phosphonomethylglycine from an aqueous solution containing N-phosphonomethylglycine and various impurities which comprises:
  A. passing the aqueous solution through a first ion exchange column containing a weakly basic ion exchange resin to remove impurities from the aqueous solution that are more acidic than N-phosphonomethylglycine;
  B. passing the aqueous solution as an effluent from the first ion exchange column through a second ion exchange column containing a weakly basic ion exchange resin until breakthrough of N-phosphonomethylglycine occurs in the aqueous solution as an effluent from the second column; and thereafter,
  C. recovering the N-phosphonomethylglycine from the weakly basic ion exchange resin in the second ion exchange column by passing a base or a strong mineral acid through the column, wherein the ion exchange resin in the first and second ion exchange columns can sorb acids having a pKa value of about 2.2 and less.

2. A method of claim 1 wherein the weakly basic ion exchange resin in the first column sorbs impurities from the aqueous solution, the impurities being selected from the group consisting of N-phosphonomethyliminodiacetic acid, N-formyl-N-phosphonomethylglycine, phosphoric acid and phosphorous acid.

3. A method of claim 1 wherein the strong mineral acid is hydrochloric acid.

4. A method of claim 1 wherein the base to recover the N-phosphonomethylglycine is selected from the group consisting of an aqueous solution of alkali metal hydroxides, alkali metal carbonates, ammonium hydroxides and ammonium carbonate.

5. A method of claim 4 wherein the alkali metal hydroxide is sodium hydroxide.

6. A method of claim 4 wherein the base is an aqueous solution of ammonium hydroxide.

7. A method of claim 1 wherein the base to recover the N-phosphonomethylglycine is an organic amine having a molecular weight below about 300.

8. A method of claim 7 wherein the organic amine is isopropylamine.

* * * * *